United States Patent [19]

Giannini

[11] Patent Number: 4,897,411

[45] Date of Patent: Jan. 30, 1990

[54] METHOD OF TREATMENT OF PREMENSTRUAL SYNDROME

[76] Inventor: A. James Giannini, 3040 Belmont Ave., Youngstown, Ohio 44505

[21] Appl. No.: 309,407

[22] Filed: Feb. 13, 1989

[51] Int. Cl.⁴ .......................................... A61K 31/415
[52] U.S. Cl. ................................................... 514/401
[58] Field of Search ........................................ 514/401

[56] References Cited

U.S. PATENT DOCUMENTS

| | | | |
|---|---|---|---|
| 3,077,437 | 2/1963 | Heckel | 167/74 |
| 4,315,033 | 2/1982 | Lawrason | 424/ |
| 4,415,554 | 11/1983 | Horrobin | 424/ |
| 4,588,739 | 5/1986 | Glassman | 424/ |

*Primary Examiner*—Stanley J. Friedman
*Attorney, Agent, or Firm*—Harpman & Harpman

[57] ABSTRACT

A method of using clonidine for the treatment of Premenstrual Syndrome (PMS) in selective subjects to reduce or alleviate subject's manifestation of psychiatric symptoms associated with PMS.

4 Claims, No Drawings

METHOD OF TREATMENT OF PREMENSTRUAL SYNDROME

BACKGROUND OF THE INVENTION

1. Technical Field

This method is directed to the treatment of Premenstrual Syndrome symptoms which by themselves as well as the clinic cyclic nature of the syndrome resembled bipolar affective disorder. To this end the neurotransmitter noreponephrine and the norepinephrine metabolite 3-methozy-4-hydrozyphenylglycol (MHPG) have been studied as possible determinants of (PMS). It has been shown that urinary MHPG levels vary in a similar fashion in both PMS and rapidcycling bipolar affective disorder. see (DeLeon-Jones F A, Steinberg J. Dekirmejian M. et al: MMPG excretion during the menstrual cycle of women. Commun Psychopharmacol 2: 227–274, 1978)

The characteristic symptoms of PMS, such as irritability, lability, anxiety, depression, and abdominal cramping are also evident in opiate withdrawal. Opiate withdrawal symptoms are believed to occur as a result of $\beta$-endorphin deregulation of norepinephrine at the locus ceruleus. see (Gold M S. Redmond D E, Kleber H D: Noradrenergic hyperactivity in opiate withdrawal. Am J Psychiatry 136: 100–103, 1979) A previous PMS study, see (Giannini A J, Price W A, Loiselle R H: Beta-endorphin levels in premenstrual distress syndrome. Int J Psychophysiol 1: 341–344, 1984) showed that the percentage of relative decrease in $\beta$-endorphin levels during the preluteal phase was inversely related to the intensity of PMS symptoms. Since it had previously been determined that opiate withdrawal, see (Gold M S, Redmond D E, Kleber H D: Noradrenergic hyperactivity in opiate withdrawal. Am J Psychiatry 136: 100–103, 1979) and bipolar affective disorders see (Giannini A J, Extein I, Gold M S, et al: Clonidine in mania. Drug Dev Res 3: 101–104, 1983 and Giannini A J, Loiselle R H, Price W A: Comparison of antimanic efficacy of clonidine and verapamil. J Clin Pharmacol 25: 307–308, 1985) both respond to clonidine, it was hypothesized that the $\beta$-endorphin regulation of norepinephrine activity at the level of the locus ceruleus was a unifying feature of both illnesses and therefore also could be applied to PMS.

SUMMARY OF THE INVENTION

The reduction and treatment of subjects symptoms associated with PMS are obtainable by the treatment of the subjects with clonidine in a symptom preventing amount for a suitable period of time. The effective amount was 17 ug/kg divided into four daily doses during the menstrual cycle.

DESCRIPTION OF THE INVENTION

A method of treating Premenstrual Syndrome (PMS) and its associated symptoms such as, but not limited to anxiety, depression, irritability, lability and abdominal cramping which has been well documented in previous studies. The method utilizes a study format of a double-blind cross over design which spanned four menstrual cycles.

Forty-seven women ranging in ages between 19 and 41 years who suffered from PMS symptoms participated in the study and gave informed consent to do so.

The diagnosis of PMS was determined on the basis of symptoms outlined in the Diagnostic and Statistical Manual, Third Edition-American Psychiatric Association (DSM-III). Nine women were eliminated due to confounding variables of affective disorder, history of medical disease or history of taking medications. The study was carried out on an outpatient basis.

Thirty-eight patients remaining in the working study were evaluated as to the severity of PMS by measuring successive levels of serum $\beta$-endorphin every 7 days over a 35 day period. It had been previously demonstrated that the rate of serum $\beta$-endorphin declined during a menstrual cycle was associated with the severity of the PMS symptoms. The rate of decline was most exaggerated during the pre-luteal phase based upon the diagnostic criteria of DSM-III and the relative criteria associated with $\beta$-endorphin levels, all women were diagnosed as having PMS.

Fourteen of the women were categorized as having only "mild" $\beta$-endorphin level decreases and were excluded from the study. The remaining 24 patients were thus indicated as having moderate or severe decreases in $\beta$-endorphin levels. These 24 women became the final working group to evaluate the effect of clonidine in reducing symptoms of the $\beta$-endorphin linked to PMS.

Two test groups were established A and B, each containing 12 patients selected by use of a random table program on a programmable calculator.

The group A subjects received clonidine at dosages of 17 ug/kg per day divided into four daily doses for two menstrual cycles. The dosage was based on previous work with manic patients and with opiate addictive patients undergoing withdrawal.

Group A subjects then received a placebo for two additional menstrual cycles.

The group B subjects received the reversed format of placebo first then clonidine in the selective doses. All subject participating medication dispensing nurses were blind to the true identity to the clonidine and placebo tablets.

Each of the patients manisfestations of psychiatric symptoms were measured on the initial day and the fifth day prior to the start of each menses using the Psychiatric Rating Scale (BPRS). The BPRS is a well accepted 7 point rating scale measuring 18 traits associated with psychopathology. The BPRS rating was conducted by a psychiatry resident blind to the true purpose of the study.

RESULTS

It will be seen that the effects of clonidine on the symptoms of PMS were analyzed with the Mann-Whitney U Test. During the first menstrual cycle (28 days), the administration of clonidine produced a significant decrease in symptoms (U=66.5, p<0.01). As clonidine was continued, these improvements continued between the first (28 days) and second (56 days) cycles (U=89, p<0.025).

When placebo was administered first, the difference between the effects of placebo and clonidine were not significant, although a strong tendency for improvement with the placebo did exist (U=117, p>0.05). When the symptoms present at the end of the fourth menstrual period (112 days) were compared with the symptoms present before placebo was administered, a significant improvement was noted (U=80.5, p<0.025). Although placebo did not produce any significant amount of improvement, the direction of improvement was consistent. When this direction was tested using the Sign test, it was found to be significant ($p<0.05$) in all cases. Thus, placebo improved PMS symptoms, although the amount of improvement was significantly ($p<0.05$) less than that produced by clonidine. It should be noted that no subject withdrew from the study.

DISCUSSION

We found that clonidine was significantly more effective than placebo in alleviating the symptoms of PMS. This drug is an $\alpha_2$-agonist that acts at the locus ceruleus by decreasing the amount of norepinephrine released at presynaptic sites. Excessive norepinephrine activity, such as is thought to occur in manic states, is sharple diminished by the use of clonidine. see (Giannini A J, Extein I, Gold M S, et al: Clonidine in mania. Drug Dev Res 3: 101–104, 1983 and Giannini A J, Loiselle R H, Price W A: Comparison of antimanic efficacy of clonidine and verapamil. J Clin Pharmacol 25: 307–308, 1985) In opiate addiction, norepinephrine is down-regulated by $\mu$-receptor sites at the locus ceruleus; these sites are activated by $\beta$-endorphin or opiate derivatives. When an opium addict's supply is suddenly cut off, the down-regulation no longer occurs and the sympathetic system is flooded with norepinephrine, which results in withdrawal symptoms. In PMS, $\beta$-endorphin levels may be significantly reduced. see (Gold M S, Redmond D E, Kleber H D: Noradrenergic hyperactivity in opiate withdrawal. Am J Psychiatry 136: 100–103, 1979) This lack of control of $\beta$-adrenergic activity may be a cause of PMS symptoms, at least in the subgroup that shows a decrease in $\beta$-endorphin levels. Thus PMS may be a phenomenon of periodic opioid withdrawal. see (Giannini A J, Price W A, Loiselle R H: Beta-endorphin levels in premenstrual distress syndrome. Int J Psychophysiol 1: 341–344, 1984 and Halbreich U, Endicott J: Possible involvement of endorphin withdrawal or imbalance in specific premenstrual syndromes and postpartum depression. Med Hypotheses 7: 1045–1058, 1981) If this is the case, then the mechanism of action that explains clonidine's effectiveness in relieving PMS symptoms is the same mechanism that accounts for clonidine's suppression of some of the symptoms of opiate withdrawal.

Clonidine's action in relieving the symptoms of PMS should be further investigated. Both the sample size and the duration of the study need to be expanded. Also, it would be useful to repeat this study, incorporating measurements of both $\beta$-endorphin and norepinephrine levels. In this way not only would the effectiveness of clonidine be further tested but more knowledge about its mechanisms of action would also be attained.

I claim:

1. A method of alleviating the symptoms of premenstrual syndrom in a patient by reducing the amount of norepinephrine released at presynoptic sites, comprising the administration to said patient of an effective amount of clonidine.

2. The method of claim 1 wherein said effective amount of clonidine is comprised of 17 ug/kg per day.

3. The method of claim 1 wherein said clonidine is used in all modalities of administration.

4. The method of claim 2 wherein said effective amounts of clonidine administered at levels of 17 ug/kg per day divided into four equal doses.

* * * * *